(12) United States Patent
Ouyang et al.

(10) Patent No.: US 12,343,248 B2
(45) Date of Patent: Jul. 1, 2025

(54) VALVED VASCULAR PROSTHESIS AND MANUFACTURING METHOD THEREOF

(71) Applicant: FUWAI HOSPITAL CHINESE ACADEMY OF MEDICAL SCIENCES, Beijing (CN)

(72) Inventors: Chenxi Ouyang, Beijing (CN); Sishi Liu, Beijing (CN); Tuo Yan, Beijing (CN); Jun Yan, Beijing (CN); Miao Yu, Beijing (CN); Huichai Li, Beijing (CN); Yuanrui Gu, Beijing (CN); Shuo Dong, Beijing (CN); Yangxue Sun, Beijing (CN)

(73) Assignee: FUWAI HOSPITAL CHINESE ACADEMY OF MEDICAL SCIENCES, Beijing (CN)

( * ) Notice: Subject to any disclaimer, the term of this patent is extended or adjusted under 35 U.S.C. 154(b) by 748 days.

(21) Appl. No.: 17/530,497

(22) Filed: Nov. 19, 2021

(65) Prior Publication Data
US 2022/0071760 A1    Mar. 10, 2022

Related U.S. Application Data

(63) Continuation of application No. PCT/CN2020/080204, filed on Mar. 19, 2020.

(30) Foreign Application Priority Data

Mar. 20, 2019  (CN) .......................... 201910210738.3

(51) Int. Cl.
*A61F 2/06*    (2013.01)

(52) U.S. Cl.
CPC ...... *A61F 2/062* (2013.01); *A61F 2220/0075* (2013.01); *A61F 2240/001* (2013.01); *A61F 2310/00005* (2013.01)

(58) Field of Classification Search
CPC .......... A61F 2/062; A61F 2/06; A61F 2/2415; A61F 2220/0075; A61F 2240/001
See application file for complete search history.

(56) References Cited

U.S. PATENT DOCUMENTS 6,454,799 B1 * 9/2002 Schreck ................ A61F 2/2433
                                          623/2.14
8,696,744 B2 * 4/2014 Matheny ............. A61L 27/3633
                                          623/2.15

(Continued)

FOREIGN PATENT DOCUMENTS

CN     101444441 B    6/2011
CN     107920885 A    4/2018

(Continued)

OTHER PUBLICATIONS

Search Report of the PCT parent application PCT/CN2020/080204 (Year: 2020).*

(Continued)

*Primary Examiner* — Jerrah Edwards
*Assistant Examiner* — Aren Patel
(74) *Attorney, Agent, or Firm* — JEEN IP LAW, LLC

(57) ABSTRACT

The present invention provides a valved vascular prosthesis and a manufacturing method thereof. The valved vascular prosthesis, comprising an artificial blood vessel and a valve disposed inside for obstruction; the valve is in a skirt state extending toward the centerline of the artificial blood vessel; the valve is made by sewing a tubular vascular material on the artificial blood vessel; one end of the vascular material is connected to the artificial blood vessel along its radial direction, and the other end is a free end; the entire tubular body of the vascular material is sewed on the artificial blood vessel by a plurality of sutures; the sutures are radially parallel to the tubular body of the vascular material, and are arranged at intervals along the circumference of the tubular (Continued)

body of the vascular material. The valved vascular prosthesis of the present invention adopts suture of a polymer material and an artificial blood vessel. When the valved vascular prosthesis is implanted into human body, the valved part is implanted together. The process is simple, easy to mold and has good biocompatibility.

6 Claims, 4 Drawing Sheets

(56) References Cited

U.S. PATENT DOCUMENTS

| | | | | |
|---|---|---|---|---|
| 2005/0027348 | A1* | 2/2005 | Case | A61F 2/2475 623/1.24 |
| 2011/0265329 | A1* | 11/2011 | Mathison | A61F 2/2415 29/890.12 |
| 2015/0018943 | A1 | 1/2015 | Paniagua et al. | |
| 2016/0100939 | A1* | 4/2016 | Armstrong | A61F 2/2418 623/2.12 |
| 2017/0065408 | A1* | 3/2017 | Grundeman | A61F 2/2412 |
| 2017/0065411 | A1* | 3/2017 | Grundeman | A61F 2/2415 |
| 2022/0071760 | A1* | 3/2022 | Ouyang | A61F 2/2415 |

FOREIGN PATENT DOCUMENTS

| | | | | |
|---|---|---|---|---|
| CN | 109893294 A | * | 6/2019 | A61F 2/062 |
| KR | 20120031649 A | * | 4/2012 | |
| WO | WO-2015169866 A1 | * | 11/2015 | A61F 2/2412 |
| WO | WO-2015169868 A1 | * | 11/2015 | A61F 2/2412 |
| WO | WO-2020187293 A1 | * | 9/2020 | A61F 2/062 |

OTHER PUBLICATIONS

International Preliminary Report on Patentability of the PCT parent application PCT/CN2020/080204 (Year: 2020).*
Written Opinion of the PCT parent application PCT/CN2020/080204 (Year: 2021).*

* cited by examiner

Step 1

Step 2

Step 3

Step 4

Step 5

Step 6

VALVED VASCULAR PROSTHESIS AND MANUFACTURING METHOD THEREOF

CROSS-REFERENCE TO RELATED APPLICATIONS

The present application is a continuation-application of International Patent Application (PCT) No. PCT/CN2020/080204 filed on Mar. 19, 2020, which claims foreign priority of three Chinese Patent Applications, No. 201910210738.3, filed on Mar. 20, 2019, the entire contents of which are hereby incorporated by reference.

TECHNICAL FIELD

The present invention relates to the technical field of artificial blood vessels, specifically, to a valved vascular prosthesis and a manufacturing method thereof.

BACKGROUND ART

Congenital heart disease is one of the most common types of congenital malformations, accounting for about 28% of various congenital malformations. At present, the incidence of congenital heart disease is increasing year by year, accounting for 0.4%-1% of the total number of living babies. Each year, there are 150,000 to 200,000 new patients in China, and about ⅓ of them have obstruction of the right or left ventricular outflow tract, such as Fallot's tetralogy, double outlet right ventricle (DORV), pulmonary artery atresia or common arterial trunk, and these patients need to reconstruct right ventricular outflow tract with valved artificial blood vessel conduits or valved vascular graft sheets.

In recent years, the research on valved vascular prostheses has become a hot spot. A number of allogenic graft materials, such as porcine aortic valve or pulmonary artery conduits, pericardial conduits, especially allogeneic animal aorta, pulmonary artery, etc. have been used in clinical practices. In 2002, Contegra pulmonary arterial valved conduits made by Medtronic's bovine jugular vein fixed with glutaraldehyde were listed in the United States through the "humanitarian exemption" way. However, it has never appeared in the Chinese markets. In china, valved conduits produced by Beijing Balance Medical Technology Co., Ltd. have been approved on the markets, similar to the Medtronic's Contegra pulmonary artery valved conduit, it is also made by bovine jugular vein after treatment with glutaraldehyde. However, more and more clinical studies show that Medtronic's Contegra products have problems such as long-term calcification of conduit wall, stenosis of distal vascular anastomosis, etc. These problems may be related to the cross-linking agent glutaraldehyde in the product molding process. Therefore, the development of a glutaraldehyde-free treatment process has become a research hotspot. At present, two products approved for marketing are made of heterogeneous animal-derived materials. But their sources are limited and they should undergo the processes of decellularization, inactivation, and fixation, etc., so the processes are complicate and the glutaraldehyde treatment is often unavoidable.

SUMMARY

An object of the present invention is to overcome the defects of the foregoing valved vascular prostheses in the prior art, and to provide a valved vascular prosthesis and a manufacturing method thereof. The valved vascular prosthesis of the present invention adopts suture of a polymer material and an artificial blood vessel. When the valved vascular prosthesis is implanted into human body, the valved part is implanted together. The process is simple, easy to mold and has good biocompatibility.

In order to achieve the foregoing object, in a basic embodiment, the present invention provides a valved vascular prosthesis, comprising an artificial blood vessel and a valve disposed inside for obstruction; the valve is in a skirt state extending toward the centerline of the artificial blood vessel; the valve is made by sewing a tubular vascular material on the artificial blood vessel; one end of the vascular material is connected to the artificial blood vessel along its radial direction, and the other end is a free end; the entire tubular body of the vascular material is sewed on the artificial blood vessel by a plurality of sutures; the sutures are radially parallel to the tubular body of the vascular material, and are arranged at intervals along the circumference of the tubular body of the vascular material.

Another object of the present invention is to provide a method for manufacturing the valved vascular prosthesis, which is the first embodiment, comprising the following steps:
S1: Prepare a vascular sheet, fold it in half, and sew multiple straight lines along the direction perpendicular to the fold line to form a valve with a row of pocket-shaped openings;
Alternatively, prepare two vascular sheets with the same or different materials; paste the two vascular sheets together and sew one side to connect the two vascular sheets, then sew multiple straight lines along the connected sides in a vertical direction, to form a valve with a row of pocket-shaped openings;
S2: Provide an artificial blood vessel, and fold one end outward along the circumferential direction so that the inner surface of the end faces outward;
S3: Sew the valve prepared in S1 on the inner surface of the artificial blood vessel that folds outwardly in a way of the pocket-shaped openings facing outward;
S4: Apply biogel to the surface of the sutures of steps S1 and S3;
S5: Fold the folded end of the artificial blood vessel inwardly to recover, to obtain a valved vascular prosthesis having a valve on the inner wall of one end of the artificial blood vessel.

In a preferred embodiment, when the two vascular sheets are sewed up in step S1, the length of the vascular sheets on both sides of the pocket-shaped opening is different, so that the pocket-shaped opening is in an open state.

In a preferred embodiment, the surface of the sutures in step S1 and step S3 are the same or similar.

In a preferred embodiment, the valve in step S1 has three pocket-shaped openings.

In a preferred embodiment, the manufacturing method further comprises step S6: providing another artificial blood vessel and sewing it on valved end of the valved vascular prosthesis obtained in step S5 to form a valved vascular prosthesis with a valve in the middle section.

In another aspect, the present invention provides a method for manufacturing the valved vascular prosthesis, which is a second embodiment, comprising the following steps:
S1: Provide an artificial blood vessel, and fold one end inward along the circumferential direction;
S2: Sew the folded part to the artificial blood vessel as a valve with three or more sutures parallel to the radial direction of the artificial blood vessel; the sutures are arranged at intervals along the circumferential direction of the artificial blood vessel; the valve is a valve chamber in a skirt shape extending along the centerline of the artificial blood vessel, having a plurality of openings;

S3: Apply biogel to the surface of the sutures of step S2, to obtain a valved vascular prosthesis having a valve on the inner wall of one end of the artificial blood vessel.

In a preferred embodiment, the manufacturing method further comprises step S4: providing another artificial blood vessel, sewing it on valved end of the valved vascular prosthesis obtained in the step S3 to form a valved vascular prosthesis with a valve in the middle section.

In the above two manufacturing methods, the material of the vascular sheet is selected from polytetrafluoroethylene, polyhexafluoropropylene, expanded polytetrafluoroethylene, polyethylene terephthalate, and polyurethane.

In another aspect, the present invention provides a valved vascular prosthesis made by the foregoing method.

Through the foregoing technical solution, the present invention obtains a valved vascular prosthesis having a valve on the inner wall of the artificial blood vessel by sewing a vascular sheet on the artificial blood vessel. The manufacturing method of the present invention is simple in process and easy to mold. During use, the valve can be implanted together with the valved vascular prosthesis; in addition, the vascular sheet may be made by different materials, so that the same valve can be made of different polymer materials to meet the needs for materials of different parts. Therefore, it can provide products with superior performance.

DETAILED DESCRIPTION OF THE EMBODIMENTS

In order to better understand the foregoing technical solutions, the technical solutions of the present invention are described by particular embodiments below. It should be understood that the embodiments of the present application and specific features in the embodiments are detailed descriptions of the technical solutions of the present application, rather than limitations on the technical solutions herein. In case of no conflict, the embodiments of the present application and the technical features in the embodiments can be combined with each other. It should be understood that the term "and/or" as used herein includes any and all combinations of one or more of the associated listed items.

In order to overcome the defects of the valved vascular prosthesis in the prior art, the embodiments of the invention adopt the following main ideas.

Figure 1:
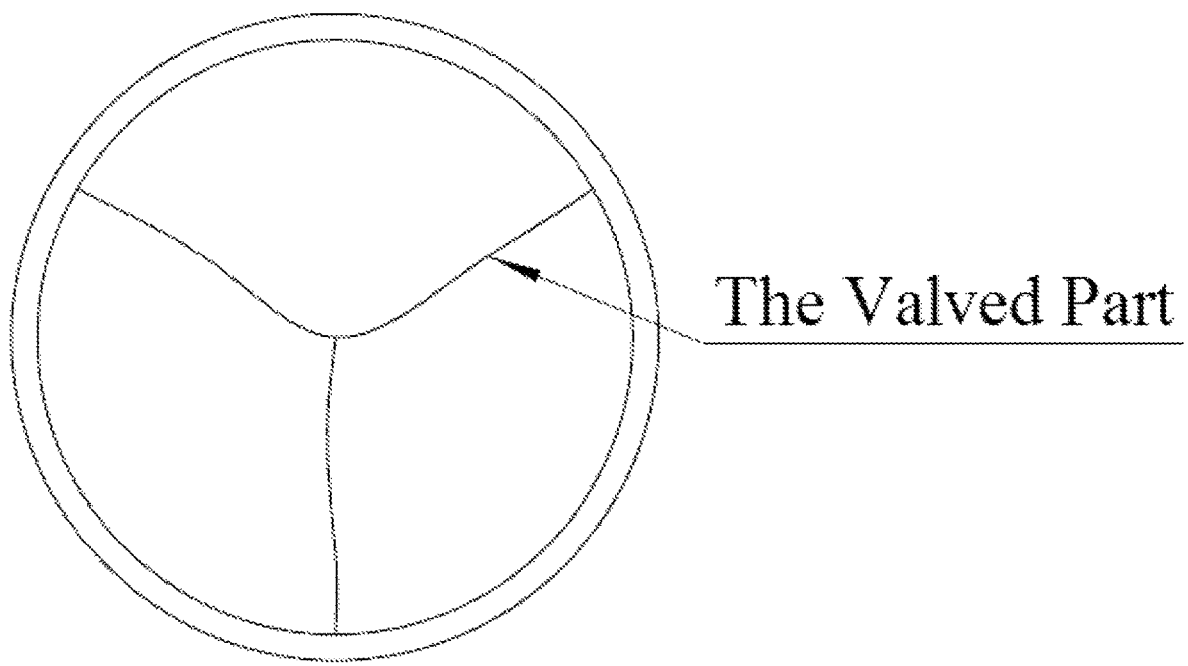
FIG. 1 is a structure diagram of a valved vascular prosthesis after molding.

A valved vascular prosthesis, as shown in FIG. 1, comprises an artificial blood vessel and a valve disposed inside for obstruction. The valve is in a skirt state extending toward the centerline of the artificial blood vessel. The valve is made by sewing a tubular vascular material on the artificial blood vessel. One end of the vascular material is connected to the artificial blood vessel along its radial direction, and the other end is a free end; the entire tubular body of the vascular material is sewed on the artificial blood vessel by a plurality of sutures, and the sutures are radially parallel to the tubular body of the vascular material, and are arranged at intervals along the circumference of the tubular body of the vascular material.

The present invention will be described in detail below with reference to specific embodiments. The materials used in the embodiments are commercially available.

Embodiment 1

Figure 2:
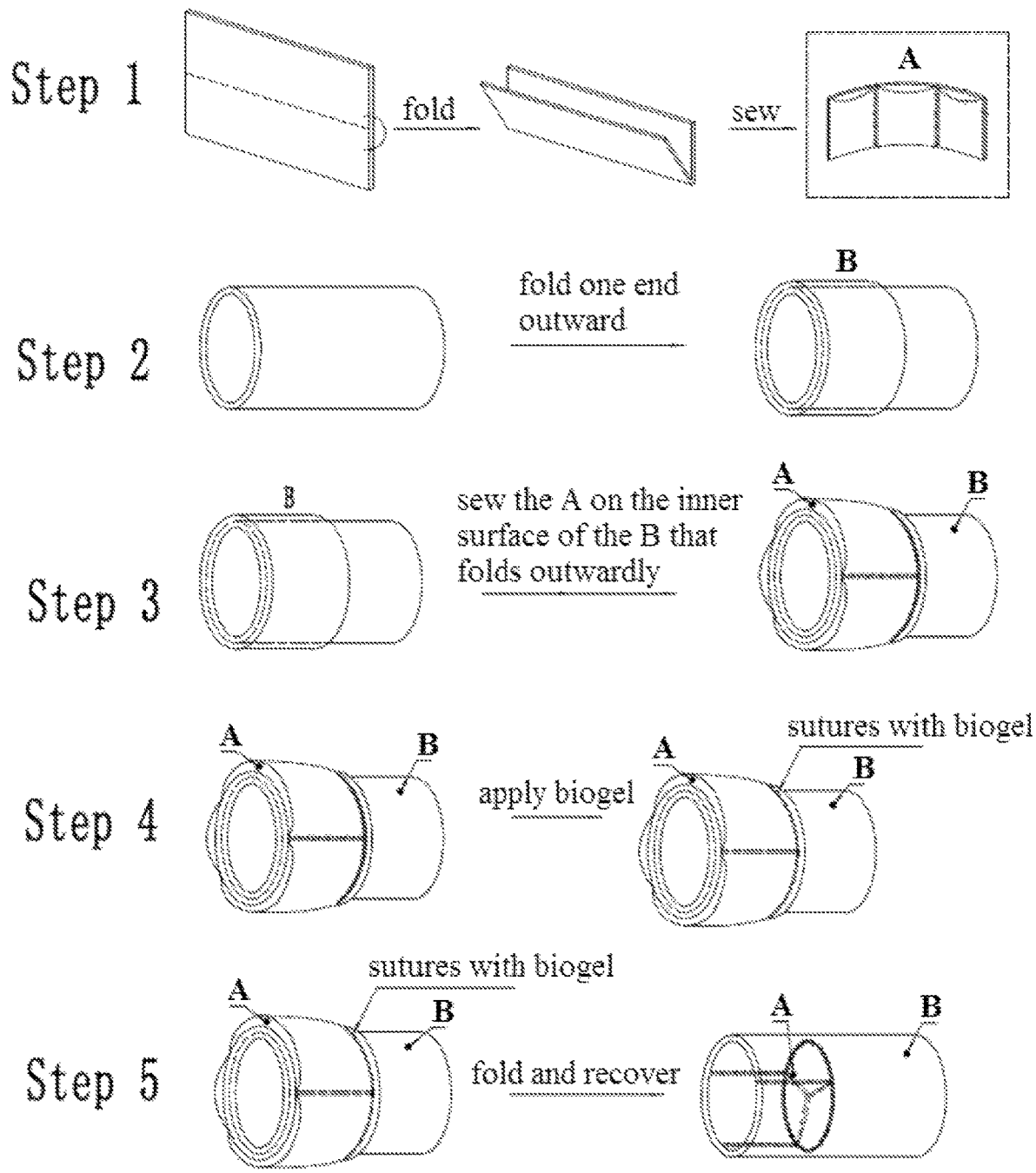
FIG. 2 is a process flow diagram of a manufacturing method of a valved vascular prosthesis according to the Embodiment 1 of the present invention.

A method of manufacturing a valved vascular prosthesis, as shown in FIG. 2, comprising the following steps:

S1: Prepare a vascular sheet (polytetrafluoroethylene PTFE material), fold it in half, and sew multiple straight lines along the direction perpendicular to the fold line to form a valve with a row of pocket-shaped openings; the valve formed after sewing in this embodiment has three pocket-shaped openings.

S2: Provide an artificial blood vessel, and fold one end outward along the circumferential direction so that the inner surface of the end faces outward.

S3: Sew the valve prepared in S1 on the inner surface of the artificial blood vessel that folds outwardly in a way of the pocket-shaped openings facing outward; sew along the direction of the circumference of the artificial blood vessel.

S4: Apply biogel to the surface of the sutures of steps S1 and S3.

S5: Fold the folded end of the artificial blood vessel inwardly to recover, to obtain a valved vascular prosthesis having a valve on the inner wall of one end of the artificial blood vessel.

Embodiment 2

Figure 3:
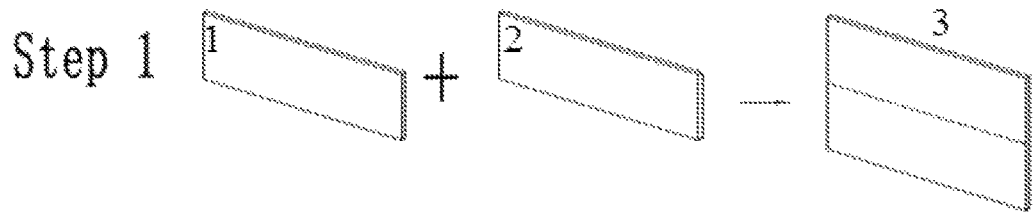
FIG. 3 is a process flow diagram of a manufacturing method of a valved vascular prosthesis according to the Embodiment 2 of the present invention.
Figure 3:
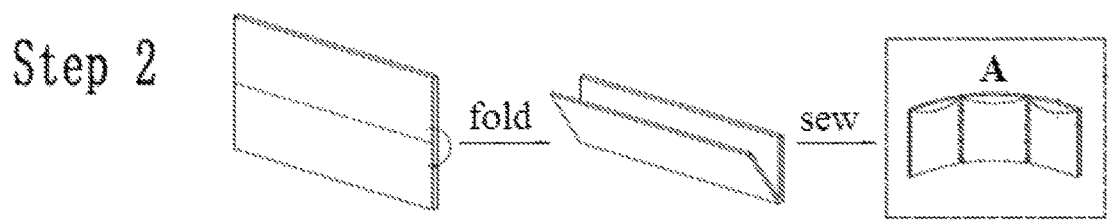
Figure 3:
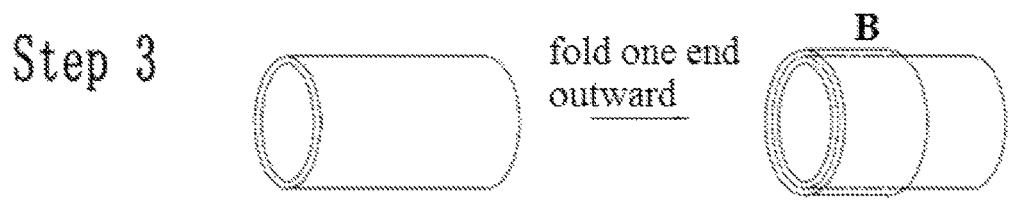
Figure 3:
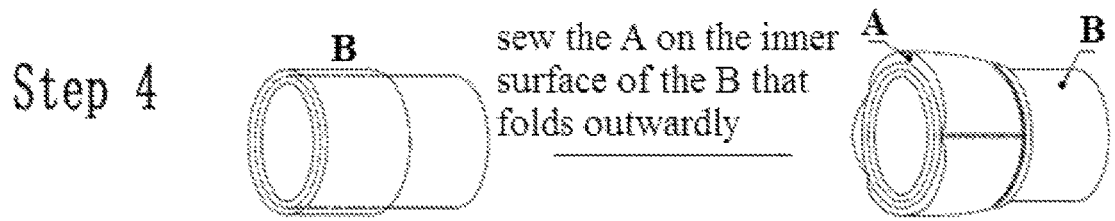
Figure 3:
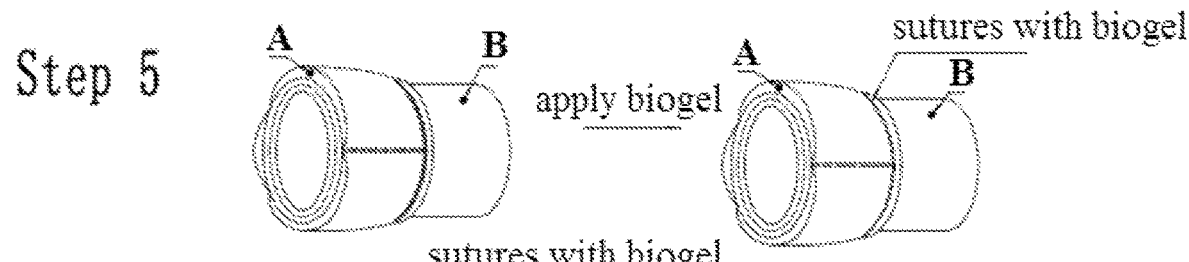
Figure 3:
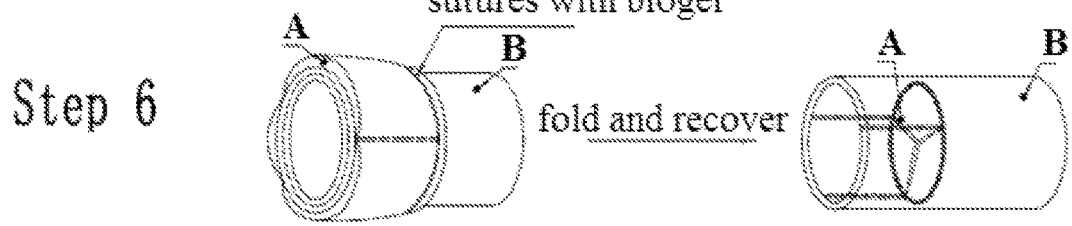

As shown in FIG. 3, this embodiment is basically the same as Embodiment 1. The difference is the step S1: prepare two vascular sheets with different materials, polyurethane (PU) and polytetrafluoroethylene (PTFE) respectively, paste the two vascular sheets together and sew one side to connect the two vascular sheets, then sew multiple straight lines along the connected sides in a vertical direction, to form a valve with a row of pocket-shaped openings. The thickness and size of the two vascular sheets may be different. When the two vascular sheets are sewed up, the length of the vascular sheets on both sides of the pocket-shaped opening may be different, so that the pocket-shaped opening is preferably in a good open state.

Embodiment 3

This embodiment is basically the same as Embodiment 2, except that the materials of the two vascular sheets are the same, which is polyethylene terephthalate (PET) material.

Embodiment 4

Figure 4:
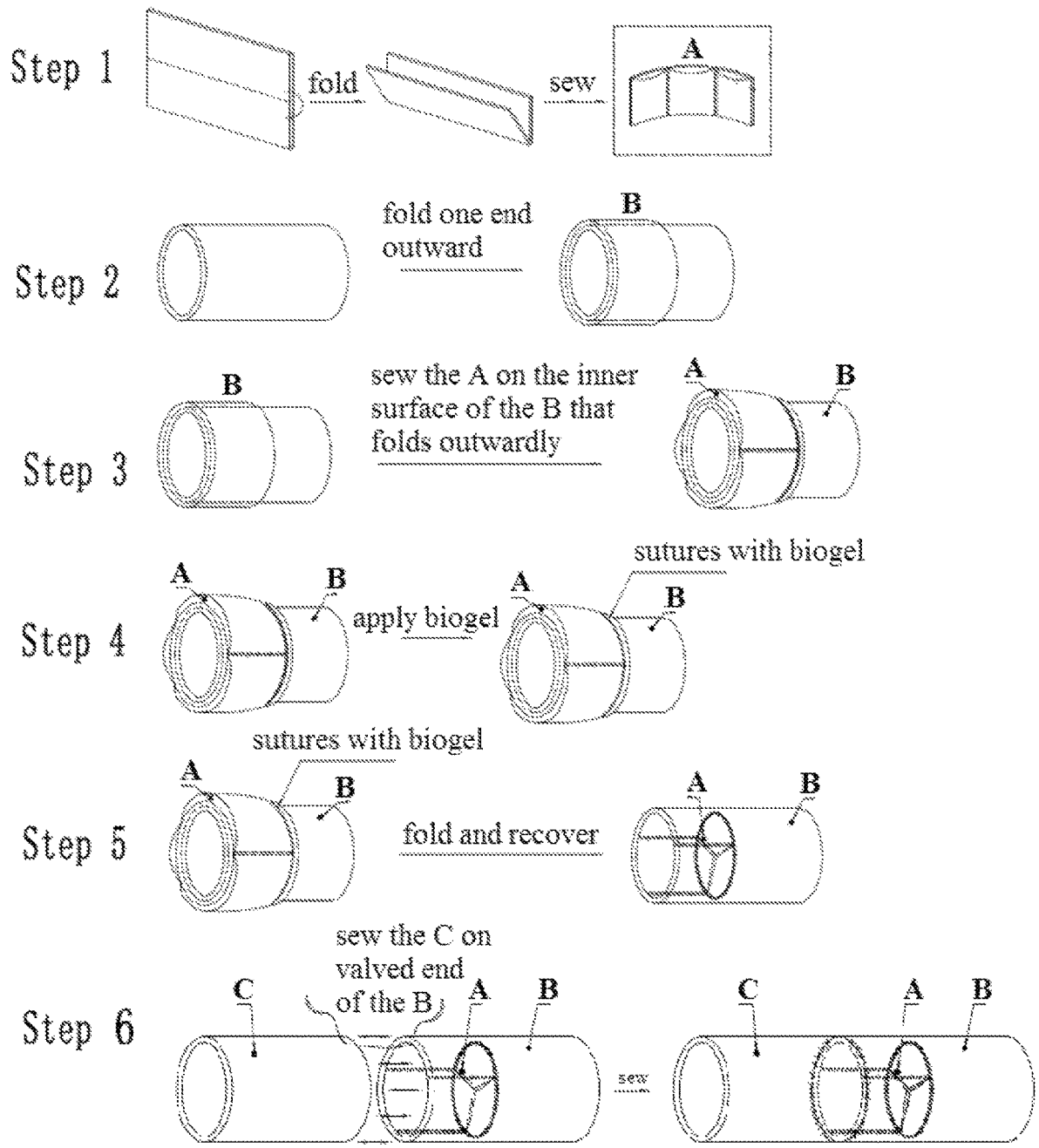
FIG. 4 is a process flow diagram of a manufacturing method of a valved vascular prosthesis according to the Embodiment 4 of the present invention.

As shown in FIG. 4, this embodiment is basically the same as Embodiment 1. The difference is that the manufacturing method further includes step S6: provide another artificial blood vessel and sew it on valved end (the end with a valve on the inner wall) of the valved vascular prosthesis obtained in the step S5, forming a valved vascular prosthesis with a valve in the middle section.

Embodiment 5

A method for manufacturing a valved vascular prosthesis, comprising the following steps:
S1: Provide an artificial blood vessel, and fold one end inward along the circumferential direction;
S2: Sew the folded part to the artificial blood vessel as a valve with three or more sutures parallel to the radial direction of the artificial blood vessel; the sutures are arranged at intervals along the circumferential direction of the artificial blood vessel; the valve is a valve chamber in a skirt shape extending along the centerline of the artificial blood vessel, having a plurality of openings;
S3: Apply biogel to the surface of the sutures of step S2, to obtain a valved vascular prosthesis having a valve on the inner wall of one end of the artificial blood vessel.
S4: Provide another artificial blood vessel and sew it on valved end of the valved vascular prosthesis obtained in the step S3, forming a valved vascular prosthesis with a valve chamber in the middle section.

The preferred embodiments of the present invention have been described in detail, but the present invention is not limited thereto. A variety of simple modifications, including the combination of various technical features in any other suitable manner, can be made to the technical solutions within the scope of the technical conception of the present invention, and these simple modifications and combinations should be regarded as the disclosure of the present invention and fall into the scope of protection of the present invention.

What is claimed is:

1. A method for manufacturing valved vascular prosthesis, comprising the following steps:
S1: Prepare two vascular sheets with different materials, paste the two vascular sheets together and sew one side to connect the two vascular sheets, forming a connecting line between the two vascular sheets, fold the two vascular sheets along the connecting line, then sew multiple straight lines along the connecting line in a vertical direction, to form a valve with a row of pocket-shaped openings;
S2: Provide an artificial blood vessel, and fold one end outward along a circumferential direction so that an inner surface of the end faces outward;
S3: Sew the valve prepared in S1 on the inner surface of the end of the artificial blood vessel that folds outwardly in a way of the pocket-shaped openings facing outward;
S4: Apply biogel to a surface of sutures of steps S1 and S3;
S5: Fold the folded end of the artificial blood vessel inwardly to an unfolded state, to obtain a valved vascular prosthesis having a valve on the inner wall of one end of the artificial blood vessel.

2. The method of claim 1, wherein the two vascular sheets are sewed up in step S1, the length of the vascular sheets on both sides of the pocket-shaped opening is different, so that the pocket-shaped opening is in an open state.

3. The method of claim 1, wherein materials of two vascular sheets are selected from polytetrafluoroethylene, polyhexafluoropropylene, expanded polytetrafluoroethylene, polyethylene terephthalate, and polyurethane.

4. The method of claim 1, wherein the surface of the sutures in step S1 and step S3 are the same or similar.

5. The method of claim 1, wherein the valve in step S1 has three pocket-shaped openings.

6. The method of claim 1, further comprising step S6: providing another artificial blood vessel and sewing it on valved end of the valved vascular prosthesis obtained in step S5 to form a valved vascular prosthesis with a valve in the middle section.

* * * * *